United States Patent [19]

Riess et al.

[11] Patent Number: 4,599,085
[45] Date of Patent: Jul. 8, 1986

[54] BONE IMPLANT MEMBER FOR PROSTHESES AND BONE CONNECTING ELEMENTS AND PROCESS FOR THE PRODUCTION THEREOF

[75] Inventors: Guido Riess; Albert Geiger, both of Garmisch-Partenkirchen, Fed. Rep. of Germany

[73] Assignee: Neodontics, Inc., Laguna Niguel, Calif.

[21] Appl. No.: 575,696

[22] Filed: Feb. 1, 1984

Related U.S. Application Data

[63] Continuation of Ser. No. 492,155, May 10, 1983, abandoned, which is a continuation of Ser. No. 168,059, Jul. 11, 1980, abandoned.

[30] Foreign Application Priority Data

Jul. 11, 1979 [DE] Fed. Rep. of Germany ....... 2928007

[51] Int. Cl.$^4$ ............ A61F 2/28; A61F 2/30; A61F 2/36
[52] U.S. Cl. ......................... 623/16; 623/18; 623/23; 128/92 B; 128/92 C; 128/92 CA; 433/173; 433/201.1
[58] Field of Search ................. 3/1.9–1.913; 128/92 C, 92 CA, 92 B; 433/173–176, 201; 623/16–23

[56] References Cited

U.S. PATENT DOCUMENTS

| | | | |
|---|---|---|---|
| 3,787,900 | 1/1974 | McGee | 433/201 X |
| 4,051,598 | 10/1977 | Sneer | 3/1.9 X |
| 4,146,936 | 4/1979 | Aoyagi et al. | 3/1.91 |
| 4,156,943 | 6/1979 | Collier | 3/1.9 |
| 4,178,686 | 12/1979 | Riess et al. | 433/201 |
| 4,309,488 | 1/1982 | Heide et al. | 3/1.9 X |

FOREIGN PATENT DOCUMENTS 2008010 8/1971 Fed. Rep. of Germany .......... 3/1.9

Primary Examiner—Ronald L. Frinks
Attorney, Agent, or Firm—Workman, Nydegger & Jensen

[57] ABSTRACT

A bone implant member for bone, joint, as well as dental prostheses, bone connecting elements such as bone screws and splints, which consists of a mechanically stable carrier material compatible (biocompatible) with bone tissue and of bioactive calcium phosphate ceramic, in particular tri- and tetracalcium phosphate, as well as a process for the production of such an implant member.

5 Claims, 5 Drawing Figures

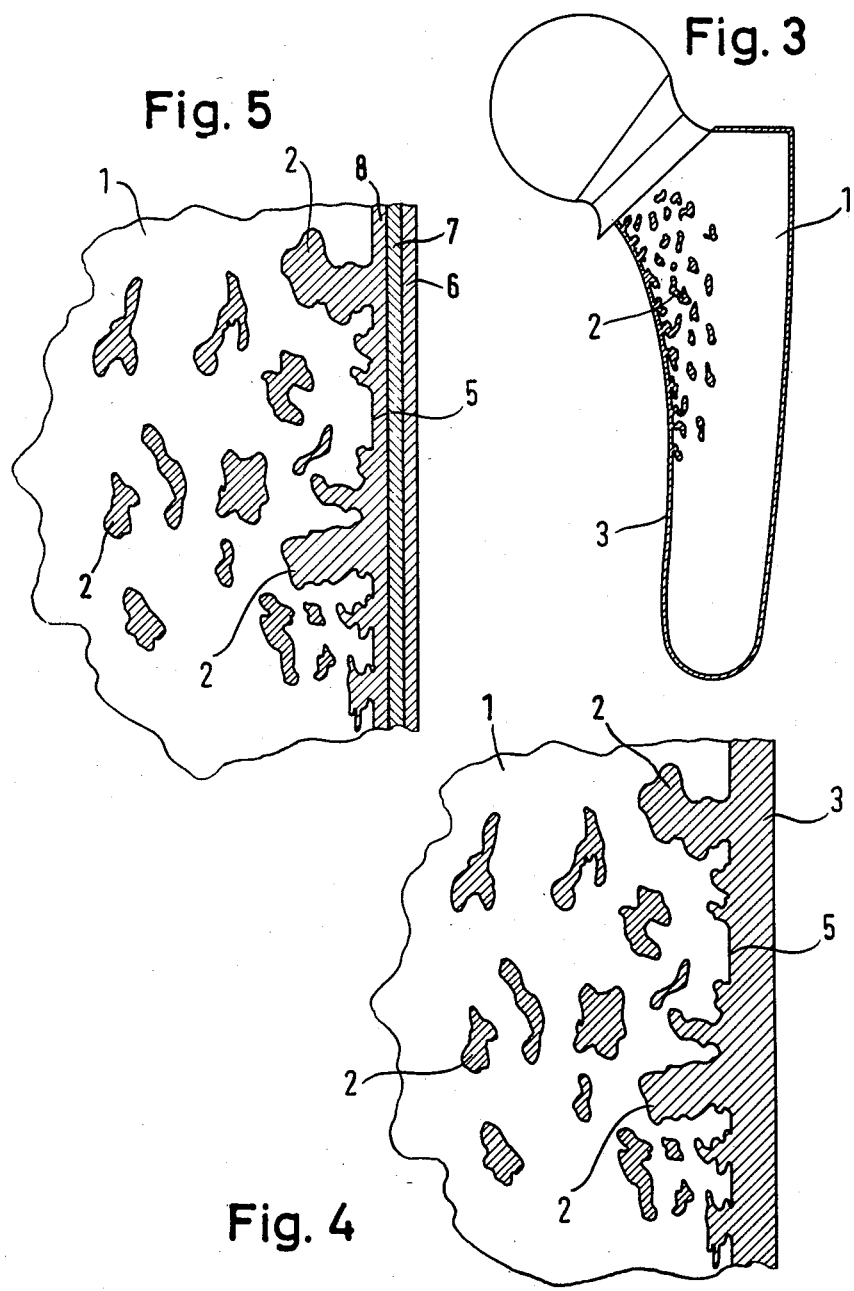

BONE IMPLANT MEMBER FOR PROSTHESES AND BONE CONNECTING ELEMENTS AND PROCESS FOR THE PRODUCTION THEREOF

This is a continuation of application Ser. No. 492,155, filed May 10, 1983, which is a continuation of application Ser. No. 168,059 filed July 11, 1980, both now abandoned.

BACKGROUND OF THE INVENTION

1. Field of the Invention

The present invention relates to a bone implant member for bone, joint, as well as dental prostheses, bone connecting elements such as bone screws and splints, which consists of a mechanically stable carrier material compatible (biocompatible) with bone tissue and of bioactive calcium phosphate ceramic, in particular tri- and tetracalcium phosphate, as well as relating to a process for the production of such an implant member.

2. Discussion of the Prior Art

Presently known and most widely utilized implants consist of an anchoring component of metal which is to be inserted in the bone and are shaped in a form of a plate, needle, screw or the like, and are predicated on a purely mechanical intermeshing with the bone in order to attain an anchoring of the prosthesis on the bone. In the interim it has been recognized that numerous technical requirements must be concurrently fulfilled with respect to the material in order to achieve a durable stable implantation. The employed materials must be biocompatible with the bone and the shaping of the implants and the mechanical properties of the material must afford a biologically correct loading and introduction of forces since, otherwise, the bone will react through degeneration and, finally, through loosening of the implant. It has further been recognized that the implant must in all regions evidence a direct, durable, osseous-like connection with the bone and cannot be encapsulated relative to the bone through a connective tissue membrane.

For this purpose, bioactive materials have become known in more recent times which effect a connective tissueless growing together of the bone with the surface of the material of the anchoring component. With such materials this relates, for example, to calcium phosphates of predetermined composition wherein there takes place a direct connective tissueless growing together of the bone with the material (Köster, "Experimenteller Knochenersatz durch resorbierbare Calciumphosphatkeramik", Langenbecks Archiv für Chirurgie 341, 77–86 (1976). These calcium phosphates are decomposable in the biological environment, in essence, they are absorbed by the cells which are active in the bone transformation, and thereby fulfill the predetermined basic biochemical condition, however, they do not come into consideration as a single material in a prosthesis which is permanently implanted due to a lack of an adequate inherent strength and due to a lack of a durable anchoring between the material of the anchoring component and the bone, because of the given reabsorbability.

In order to create a permanent anchoring for extensively loaded implants which will lead to a really permanent interconnection between the prosthesis and the tissue, it has become known from German-Laid Open Patent Application No. 26 20 907 that the anchoring of the prosthesis can be constructed as a prosthesis shaft coating from a plastic material which is mechanically and chemically stable in the environment of the body, and to so deposit therein ceramic calcium phosphate in a particulate form of predetermined particle size diameter so that there is produced a generally porous matrix of plastic material during the reabsorption of the ceramic components on whose inner pore surfaces there remain bioactivated residues of the ceramic.

In accordance with another proposal for an implantable tooth root as disclosed in German-Laid Open Patent Application No. 27 33 394, this essentially consists of a biostable polymer matrix which is compatible with human cell tissue, in which there are deposited the reabsorbable bioreactive calcium phosphate in a finely-dispersed form, which are encompassed by a thin, porous layer of nonreabsorbable calcium phosphate, and in which there is inserted a core as a connecting element for the mounting of a dental superstructure.

However, some hesitations exist in connection with the utilization of plastic materials in the form of a polymer matrix as a carrier member for the ceramic calcium phosphate although, at this time, they are still well employed in practice. Polymer plastics frequently also include monomers in other deleterious materials which in implants, after respective aging, can lead to exchange reactions with the tissue. Moreover, a plastic material carrier member does not allow for a sufficiently precise shaping and mechanical working in order to enable the construction of an implant equipped with a plastic material support member for the most different purposes, such as bone and joint protheses, or also for bone connecting elements, such as screws, splints and the like.

SUMMARY OF THE INVENTION

Accordingly, it is an object of the present invention to provide a bone implant member and, particularly, a connecting material for implant members of that type, concerning which there are no objections regarding their permanent biocompatibility, and which can be produced in all desired configurations with adequate precision and which can be mechanically worked.

In order to attain the foregoing object there is proposed a bone implant member of the above-mentioned type, which is characterized in that the support or carrier material is a biocompatible metal, such as titanium, tantalum, niobium or a similar harmless sintered metal which is capable of bonding with calcium phosphate ceramic without the formation of intermediate reaction products. A prerequisite for the metals employed is a proven biocompatibility and minimum corrosion in the bone tissue. Momentarily, titanium is the metal which most closely fulfills these requirements. It has been found that calcium phosphate ceramics which are present as a powder in a finely-dispersed up to lumpy form, can be combined with titanium powder of a somewhat similar grain size into a compound material through a pressing or sintering process, which evidences the physical and chemical advantages of the sum of the individual materials. Achieved are the physical advantages of the metal, in this instance titanium with its lack of corrosion, physical stability and relatively high biocompatibility, and also achieved are the biochemical advantages of the calcium phosphate ceramic, in particular the tricalcium phosphate, in its bioactive reabsorbability. Thus, this principle of the combination effect of the heretofore utilized plastic material-compound materials of calcium phosphate ceramics with polymers is known. However, the previously mentioned objections are present as concerns the polymer plastics. Until the present it has not been considered to be possible to also combine metals with calcium phosphate ceramics into a unitary, mechanically stable member with the retention of the bioactive properties of the calcium phosphate. The advantage of the application of metals as the support or carrier material lies in the higher and calculable long-term stability in the bone tissue. Moreover, titanium has proven itself over an investigative period of almost twenty years to be the best compatible metal within the bone tissue. The corrosion content is relatively low and, consequently, the biochemical rejection potential is small.

A process for the production of an inventive implant member is thus characterized in that a powder of the biocompatible metal is admixed with a finely-dispersed up to lumpy available calcium phosphate ceramic and, through sintering under high pressure, are interconnected with each other. Suitably, metal powder and calcium phosphate ceramic of generally the same grain size are admixed with each other in a somewhat equal volumetric ratio (spacial filling), and then sintered. The sintering temperature lies within a range of over 1500° K. (degrees Kelvin) up to 2300° K. in conformance with the intended sintering density of the calcium phosphate support member. The lower there can be held the sintering temperature, the better is the reabsorbability of the calcium phosphate ceramic. The high pressure concurrently applied with the sintering process lies at about $10^6$ kPa (10,000 bar). Desired in the interior of the sintered together implant member is a poorer reabsorbability but a greater form stability therefor. Through respective control over the sintering process, in essence, introduction of the components, is it possible to essentially arrange or enrich the calcium phosphate ceramic in the region of the surface of the metal or sintered metal member.

In a particularly advantageous embodiment of the invention, the implant member includes, at least at the sides facing towards the bone surface in the implant space within the bone, a surface layer consisting completely of calcium phosphate, particularly tricalcium phosphate. Due to obtained experimental and clinical experiences, the pure calcium phosphate surface layer should have the thickness of about 0.1 to 0.5 mm. Inventively, the surface layer of pure calcium phosphate is pressed on the implant member through the intermediary of a further pressure-sintering process. The thereon sintered tricalcium phosphate surface layer is homogeneously interconnected with the calcium phosphate particles containing metal-calcium phosphate in the compound material whereas, in the compound material itself, there is present more than one mechanical bond between metal and calcium phosphate, so that the tricalcium phosphate surface layer is present in a fixed bonded formation with the support member. Heretofore, ceramic coatings could only be applied to metal by a flaming process through strong adhesion by means of oxide layers and adhesive media. Through the inventive compound material there are present calcium phosphate regions which are bonded within a metal support or carrier, on which there can be directly and fixedly anchored in an ideal manner the surface layer of pure calcium phosphate. Sought for the tissueless ingrowth of the bone tissue has been such a pure calcium phosphate contact layer. Until the present it has only been possible to apply calcium phosphate coatings on polymer compound materials or on glass ceramic.

In a further modification of the invention, the surface layer is reabsorbable in the region of its exterior surface through degraduatingly applied sintering pressures and, with increasing depth relative to the implant member, is always less reabsorbable until completely nonreabsorbable. The production of such a surface layer is inventively achieved through impressing of the surface layer by means of sequentially degraduating pressure-sintering processes, by means of which the surface layer in the region of its outer surface remains reabsorbable due to relatively low sintering temperatures, and with increasing depth relative to the implant support becomes always less reabsorbable until completely nonreabsorbable due to higher sintering temperatures.

In another especially advantageous embodiment of the invention, the surface layer consists of a plurality of different highly sintered or different highly pressed superimposed calcium phosphate layers, wherein the outer layer consists of pure low sintered, good reabsorbable tricalcium phosphate, a middle layer which retards the bone growth consists of highly sintered, difficulty reabsorbable up to nonreabsorbable tricalcium phosphate, and an inner support layer of nonreabsorbable, highly sintered calcium phosphate. Hereby, suitably, the innermost support layer can also be constituted of non-reabsorbable tetracalcium phosphate, occasionally in admixture with highly sintered tricalcium phosphate. The formation of these individual, superimposed calcium phosphate layers of the surface layer is inventively attained through impression in sequentially-effected pressure-sintering sequences, in which the inner support layer and the retarding layer are pressed on at comparatively high sintering temperatures and/or pressures, and the outer layer is pressed on at a comparatively lower sintering temperature.

The last-mentioned embodiment of the invention intends as its object that, independently of the adhesion of the calcium phosphate layers to the support material, there is created a reduced reabsorbability with a herein so-called growth retardant for the bone. It is essential that the bone growth comes to a standstill after the reabsorbing of the outer surface layer of easily reabsorbable tricalcium phosphate in a pure calcium phosphate layer (retardant layer) which faces towards the bone, and any solubility is reduced to a minimum. The quantity of the remaining retardant layer and the support layer of nonreasborbable, highly sintered tricalcium phosphate or of nonreabsorbable tetracalcium phosphate arranged therebelow serve the bone in its periodic reabsorption, occasionally reoccuring after years, as retardant and support layer remaining as calcium phosphate reservoir impart to the bone tissue the capability of a renewed disassociation and a boundary layer metamorphosis with calcium and phosphate ions. The lowermost, nonreabsorbable support layer can also be designated as a pure insulating layer, in particular also for the instance of an aggressive reabsorption in youthful bone.

Under the term highly sintered tricalcium there is to be understood that this is pressed on at temperatures of above 2100° K. Under a low sintered calcium phosphate layer there is to be understood herein that this pertains to a layer pressed on under a temperature of below about 1900° K.

The range utilization of this inventive bonding material is the entire field of dental implantology, in essence, the collective shapes which can be produced thereby, as well as their ancillary areas. This signifies that root pins, transfixing pins, and bone splints can be produced in this manner. Moreover, this compound material extends itself into the sphere of the entire orthopedic surgery up to bone screws. The inventive compound material can be sintered onto known core structures (metal members for hip joint protheses, bone screws and the like).

The advantage of the inventive compound material is: normalized produceability of the shapes, graceful configuration of the implant members, bioreactive behavior of the implant member surface in the bone tissue, relatively simple and economic production of the implant members.

Relative to the microstructural construction of the material there can be indicated the following: the physical-chemical bonding of calcium phosphates and the above-mentioned metals capable of sintering has been proven. Obtained is a marbelized microstructural and finely porous material structure which withstands the required mechanical loads. The applied calcium phosphate layer as a surface layer will especially adhere to the calcium phosphate particles, but it is also to be pressed onto the metals capable of sintering and undergoes a stable bonding therewith.

BRIEF DESCRIPTION OF THE DRAWINGS

Reference may now be had to the accompanying drawings showing illustrative embodiments of bone implant members constructed from the inventive compound material; in which:

FIG. 3 schematically shows a partially sectioned view through a hip joint prosthesis;

FIG. 4 schematically illustrates, in an enlarged scale, a sectional view through the edge region of an implant member; and FIG. 5 shows, in an enlarged scale, a sectional view through the edge region of another embodiment of the implant member.

DETAILED DESCRIPTION

Figure 1:
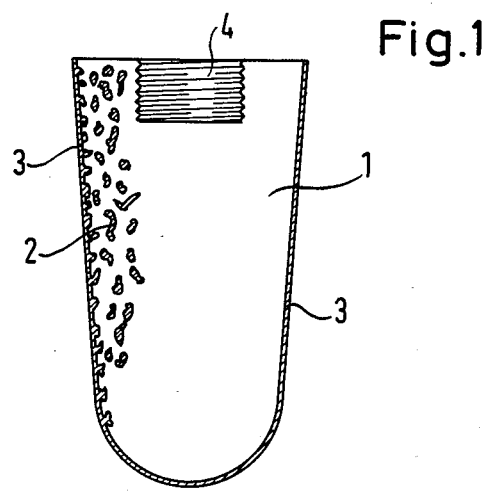
FIG. 1 schematically illustrates a cross-sectional view through a dental implant.

The dental implant member pursuant to FIG. 1 consists of a metal-calcium phosphate ceramic-sintered compound material 1 in which the illustrated metal areas are shown in white and the calcium phosphate areas which are introduced through sintering are cross-hatched and are designated with reference numeral 2. For purposes of clarity the calcium phosphate inclusions 2 are only drawn in over a partial area although they extend over the entire compound material 1. The implant member is provided with a surface layer 3 of pure calcium phosphate ceramic, whose thickness in the drawing is shown extensively exaggerated. Correspondingly, the calcium phosphate inclusions 2 are shown at an extensive exaggeration which does not conform to the actual microscopic image. In its upper region, the implant member is provided with a threaded recess 4 for the receipt and fastening of a dental superstructure, such as a tooth, bridge or the like.

Figure 2:
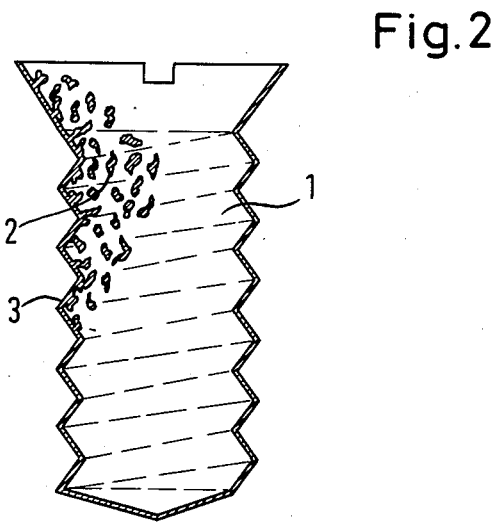
FIG. 2 schematically illustrates a cross-sectional view through a bone screw.

The bone screw illustrated in FIG. 2 consists of the same compound material 1 with inserted calcium phosphate areas 2 and a surface layer 3. The type of production and size corresponds to FIG. 1.

FIG. 3 schematically illustrates a hip joint prosthesis formed of the inventive compound material 1 with calcium phosphate inclusions 1 and a surface layer 3 of pure calcium phosphate. The manner of formulation corresponds to that in FIG. 1.

Illustrated in FIG. 4 in an extensively enlarged scale is the manner in which the surface layer 3 of pure calcium phosphate is homogenously anchored with the compound material 1 through the free calcium phosphate inclusions 2 lying on the surface 5 of the material 1. In order to clarify the size of magnitude it is noted that the surface layer 3 is approximately 0.1 to 0.5 mm thick.

In the embodiment shown in FIG. 5, the surface layer consists of pure calcium phosphate formed of a plurality of different highly sintered or differently highly pressed superimposed calcium phosphate layers, in essence, an outer layer 6, a middle layer which retards the bone growth which is the so-called retarding layer 7, and an inner support of carrier layer 8. The biocompatible material forming the support material may also be selected from materials consisting of titanium, gold, platinum, stainless steel or any other similar harmless sintered metal bondable to calcium phosphate ceramic without the formation of interreaction products.

What is claimed is:

1. A bone implant member capable of being used for bones, joints, dental prosthesis, bone screws and splints, and other bone connecting elements, said bone implant member being fashioned at least in part of a compound consisting essentially of a substantially homogeneous sintered mixture of:

(a) a bioreactive, particulate calcium phosphate ceramic, said ceramic consisting essentially of a mixture of tricalcium phosphate and tetracalcium phosphate; and (b) a biocompatible, mechanically stable, particulate metal;

wherein the bone implant member is formed by admixing the particulate calcium phosphate ceramic and the particulate metal and bonding the particulate calcium phosphate ceramic and the particulate metal by sintering under high pressure whereby the particulate metal is substantially homogenously distributed throughout the sintered bone implant member.

2. A bone implant member as defined in claim 1 further comprising:

a layer of substantially pure calcium phosphate formed on at least a portion of the outer surface of the bone implant member, said layer of calcium phosphate being anchored to the bone implant member by a bond formed between the calcium phosphate layer and the particulate calcium phosphate ceramic of the member.

3. A bone implant member as defined in claim 2 wherein the particulate calcium phosphate ceramic particles and the particulate metal particles are substantially equal in size and are mixed together in substantially equal volumetric portions.

4. A bone implant member as defined in claim 2 wherein the particulate metal is selected from the group consisting of titanium, platinum, gold, and stainless steel.

5. A bone implant member as defined in claim 2 wherein the particulate metal is selected from the group consisting of tantalum and niobium.

* * * * *

UNITED STATES PATENT AND TRADEMARK OFFICE
CERTIFICATE OF CORRECTION

PATENT NO.   :   4,599,085

DATED        :   July 8, 1986

INVENTOR(S)  :   Guido Riess et al.

It is certified that error appears in the above-identified patent and that said Letters Patent is hereby corrected as shown below:

```
    Column 1, line 53, "environment, in essence" should be
--environment; in essence--
    Column 1, line 56, "condition, however" should be --condition.
However--
    Column 2, line 13, "are" should be --is--
    Column 2, line 15, "are" should be --is--
    Column 4, lines 30-31, "sequentially-effected" should be
--sequentially affected--
    Column 4, line 50, "reoccuring" should be --recurring--
    Column 5, line 18, "marbelized" should be --marbleized--
    Column 5, line 30, "material; in which:" should be
--material, in which:--
    Column 6, line 16, "differently highly pressed" should be
--different highly pressed--
```

Signed and Sealed this

Twenty-third Day of September 1986

[SEAL]

Attest:

DONALD J. QUIGG

Attesting Officer

Commissioner of Patents and Trademarks